(12) United States Patent
Desmurs et al.

(10) Patent No.: US 6,348,631 B1
(45) Date of Patent: Feb. 19, 2002

(54) METHOD FOR ACYLATION OR SULPHONYLATION OF AN AROMATIC COMPOUND

(75) Inventors: Jean-Roger Desmurs, Saint Symphorien d'Ozon; Jacques Dubac, Pechbusque; Andre Laporterie, Pompertuzat; Christian Laporte, Mielan; Julien Marquie, Lannemezan, all of (FR)

(73) Assignee: Rhodia Chimie, Courbevoie Cedex (FR)

( * ) Notice: Subject to any disclaimer, the term of this patent is extended or adjusted under 35 U.S.C. 154(b) by 0 days.

(21) Appl. No.: 09/367,603
(22) PCT Filed: Mar. 11, 1998
(86) PCT No.: PCT/FR98/00497
§ 371 Date: Nov. 22, 1999
§ 102(e) Date: Nov. 22, 1999
(87) PCT Pub. No.: WO98/40339
PCT Pub. Date: Sep. 17, 1998

(30) Foreign Application Priority Data

Mar. 12, 1997 (FR) ............................................. 97/02917

(51) Int. Cl.$^7$ ............................. C07C 45/46; C07F 1/00
(52) U.S. Cl. ...................... 568/319; 568/322; 568/323; 204/157.6; 204/157.93
(58) Field of Search ................................ 568/319, 322, 568/323; 204/157.6, 157.93

(56) References Cited

U.S. PATENT DOCUMENTS 4,895,984 A * 1/1990 Eggersdorfer et al. ...... 568/319

FOREIGN PATENT DOCUMENTS

FR  2 722 781  1/1996

OTHER PUBLICATIONS

Chemical Abstracts, vol. 112, No. 24, Jun. 11, 1990, Columbus, Ohio, US; Abstract No. 220059, Bailey N.T. et al, "The use of microwave heating in the acetylation of coals" XP002045937, see abstract & Fuel (Fuelac, 00162361); 90; vol. 69 (4); pp. 533–534, Univ. Birmingham; Sch. Chem. Eng.; Birmingham; B15 2 TT; UK (GB).

Patent Abstracts of Japan, vol. 018, No. 462 (C–1243), Aug. 29, 1994 & JP 06 145200 A (Maruha Corp), May 24, 1994, see abstract.

El 'Tsov A.V. et al, "Sulfonation and desulfonation of naphthalene under conditions of microwave activation", Russ. J. Gen. Chem. (RJGCEK, 10703632);97; vol. 67 (2); pp. 295–299, St. Petersburg State Institute Of Technology; St. Petersburg; Russia (RU), XP002070105, see p. 298–p. 299 (1997).

Chemical Abstracts, vol. 127, No. 9, Sep. 1, 1997, Columbus, Ohio, US; Abstract No. 121537, Brykov A.S. et al, "Sulfonation of aromatic amines during microwave heating" XP002070106 & ZH. Prikl. Khim. (S.–Peterburg) (Zpkhab, 00444618); 97; vol. 70(3); pp. 514–516, St. Peterburg. Tekhnol. Inst.; St. Petersburg; Russia (RU).

* cited by examiner

Primary Examiner—Sreeni Padmanabhan
(74) Attorney, Agent, or Firm—Burns, Doane, Swecker & Mathis, L.L.P.

(57) ABSTRACT

The present invention relates to a process for the acylation or sulphonylation of an aromatic compound.

More particularly, the invention relates to a process for the acylation or sulphonylation of an activated or deactivated aromatic compound.

The invention is applied to the preparation of aromatic ketones or sulphones.

The process for the acylation or sulphonylation of an aromatic compound which consists in reacting at least one aromatic compound with an acylating or sulphonylating agent, in the presence of a Friedel-Crafts catalyst is characterized in that the acylation or sulphonylation reaction is carried out in liquid phase under microwave irradiation.

40 Claims, No Drawings

METHOD FOR ACYLATION OR SULPHONYLATION OF AN AROMATIC COMPOUND

This application is a 371 of PCT/FR98/00497 filed Mar. 11, 1998.

The present invention relates to a process for the acylation or sulphonylation of an aromatic compound.

To be more exact, the invention relates to a process for the acylation or sulphonylation of an activated or deactivated aromatic compound.

It is of particular interest in the case where the acylation or sulphonylation of a deactivated aromatic compound is desired.

The invention is applied to the preparation of aromatic ketones or sulphones.

In the following description of the present invention, "aromatic compound" is understood as meaning the conventional concept of aromaticity as defined in literature, in particular by Jerry MARCH, Advanced Organic Chemistry, $4^{th}$ edition, John Wiley and Sons, 1992, pp. 40 et seq. "Deactivated aromatic compound" is defined as an aromatic compound without a substituent, such as, for example, benzene, or an aromatic compound containing one or more substituents which deactivate the aromatic nucleus, such as electron-withdrawing groups. "Activated aromatic compound" describes an aromatic compound which contains one or more substituents which activate the aromatic nucleus, such as electron-donating groups.

The concepts of electron-withdrawing groups and electron-donating groups are defined in literature. Reference may be made, inter alia, to the work by Jerry MARCH— Advanced Organic Chemistry, $4^{th}$ edition, John Wiley and Sons, 1992, chapter 9, pp. 273–292.

A conventional process for the preparation of aromatic ketones comprises reacting an aromatic compound and an acylating agent by an acylation reaction of the Friedel-Crafts type.

It is thus known to carry out said reaction in the presence of catalysts such as: $FeCl_3$, Fe, $ZnCl_2$, $I_2$ [D. E. PEARSON, C. A. BUEHLER, Synthesis, 1972, p.533]; metallic trifluoromethanesulphonates [A. KAWADA et al., J. Chem. Soc. Chem. Commun. pp. 1157–1158 (1993) and Synlett pp. 545–546 (1994)]; bismuth halides or precursors [EP-A-698 593].

The reactions described are limited to activated aromatic compounds, such as anisole, and most often require very long reaction times.

In the case of deactivated aromatic substrates, such as benzene or the halogenobenzenes, these catalysts are not satisfactory.

However, $FeCl_3$ has been described for carrying out the benzoylation of benzene (FR-A-2 534 905 and FR-A-2 534 906), but the experimental conditions are then restricting. The reaction is carried out in an autoclave in the presence of 8% $FeCl_3$: the yield is only 56% after heating at 145° for 2 h.

D. E. PEARSON et al. [op. cit.] report some exceptional results of acylation of aromatic compounds in the absence of catalysts by a simple thermal effect, but the reaction times are very long and the yields remain low, in particular in the case of deactivated aromatic compounds.

These last references, like the number of catalysts described in the prior art, do not relate in a general manner to the problem of the acylation of both activated and deactivated aromatic substrates under conditions which are easily implemented.

The present invention achieves this objective and provides a process which allows the above-mentioned disadvantages to be prevented.

A process for the acylation or sulphonylation of an aromatic compound has now been found, which is the object of the present invention, which comprises reacting said aromatic compound with an acylating or sulphonylating agent in the presence of a Friedel-Crafts catalyst, characterised in that the acylation or sulphonylation reaction is carried out in a liquid phase under microwave irradiation.

According to the process of the invention, the preparation of an aromatic ketone or aromatic sulphone is carried out by the Friedel-Crafts reaction under microwave radiation under conditions which are greatly improved with respect to those which have been known.

It is possible to carry out the acylation or sulphonylation of activated, non-activated or deactivated aromatic compounds in an open reactor.

The reaction times are very short, and are distinctly lower than the reaction times used under a simple thermal effect in the presence of the same catalysts, and with reaction yields which are often higher.

A considerably reduced consumption of electrical energy comparied with the use of an electric resistance furnace, both in the power required (60 to 300 watt instead of several kilowatt) and in the very much shorter reaction times, is also noted.

To be more exact, the present invention relates to a process for the acylation or sulphonylation of an aromatic compound corresponding to the general formula (I):

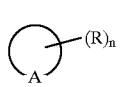

(I)

in which:

A symbolizes the residue of a ring which forms all or part of a monocyclic or polycyclic, aromatic carbocyclic or heterocyclic system; it being possible for said cyclic residue to carry a radical R representing a hydrogen atom or one or more identical or different substituents, n represents the number of substituents on the ring.

The invention is applied, in particular, to aromatic compounds corresponding to the formula (I) in which A is the residue of an optionally substituted cyclic compound preferably having at least 4 atoms in the ring, representing at least one of the following rings:

a monocyclic or polycyclic, aromatic carbocyclic ring, a monocyclic or polycyclic, aromatic heterocyclic ring containing at least one of the heteroatoms O, N and S.

It may be said, but without limiting the scope of the invention, that the optionally substituted residue A represents the residue:

1. —of a monocyclic or polycyclic, aromatic carbocyclic compound.

"Polycyclic carbocyclic compound" is understood as meaning:

a compound made up of at least 2 aromatic carbocyclic rings which form with one another ortho- or ortho- and pericondensed systems, a compound made up of at least 2 carbocyclic rings, only one of which is aromatic and which form with one another ortho- or ortho- and pericondensed systems.

2. —of a monocyclic or polycyclic, aromatic heterocyclic compound.

"Polycyclic heterocyclic compound" is defined as:
- a compound made up of at least 2 heterocyclic rings containing at least one heteroatom in each ring, at least one of which two rings is aromatic and which form with one another ortho- or ortho- and pericondensed systems,
- a compound made up of at least one hydrocarbon ring and at least one heterocyclic ring, at least one of which rings is aromatic and which form with one another ortho- or ortho- and pericondensed systems.

3. —of a compound made up of a chain of rings, as defined in paragraphs 1 and/or 2, bonded to one another:
   - by a valency bond,
   - by an alkylene or alkylidene radical having 1 to 4 carbon atoms, preferably a methylene or isopropylidene radical,
   - by one of the following groups:

—O—, —CO—, —COO—, —OCOO—
—S—, —SO—, —SO$_2$—,

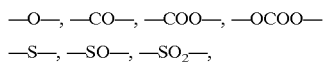

In these formulae, $R_o$ represents a hydrogen atom or an alkyl radical having 1 to 4 carbon atoms, a cyclohexyl or phenyl radical.

More particularly, the residue A which is optionally substituted represents the residue:
- of an aromatic, carbocyclic, monocyclic compound, such as benzene, toluene, isobutylbenzene, anisole, thioanisole, phenetole or veratrole, guaiacol, guetol, mono- and dichlorobenzenes, fluorobenzene, iodobenzene,
- of an aromatic, condensed, polycyclic compound, such as naphthalene, 2-methoxynaphthalene, 3-methoxynaphthalene,
- of an aromatic, carbocyclic, non-condensed polycyclic compound, such as phenoxybenzene,
- of a partially aromatic, carbocyclic, condensed, polycyclic compound, such as tetrahydronaphthalene, 1,2-methylene dioxybenzene,
- of a partially aromatic, carbocyclic, non-condensed, polycyclic compound, such as cyclohexylbenzene,
- of an aromatic, heterocyclic, monocyclic compound, such as pyridine, furane, thiophene,
- of a partially heterocyclic, aromatic, condensed, polycyclic compound, such as quinoline, indole or benzofurane,
- a partially heterocyclic, aromatic, non-condensed polycyclic compound, such as phenylpyridines, naphthylpyridines,
- of a partially heterocyclic, partially aromatic, condensed, polycyclic compound, such as tetrahydroquinoline,
- of a partially heterocyclic, partially aromatic, non-condensed, polycyclic compound, such as cyclohexylpyridine.

In the process of the invention, use is preferably made of an aromatic compound of formula (I) in which A represents a benzene or naphthalene nucleus.

The aromatic compound of formula (I) can carry one or more substituents.

The number of substituents present on the ring depends on the carbon condensation of the ring and on the presence or absence of unsaturations on the ring.

The maximum number of substituents which can be carried by a ring is easily determined by the person skilled in the art.

In the present text, "several" is generally understood as meaning less than 4 substituents on an aromatic nucleus. Examples of substituents are given below, but this list is not limiting in character. As mentioned above, the substituents may or may not activate the aromatic nucleus.

The residue A can optionally carry one or more substituents represented in the formula (I) by the symbol R, the preferred meanings of which are defined below:

the radical or radicals R represents/represent one of the following groups:
- a hydrogen atom,
- a linear or branched allyl radical having 1 to 6 carbon atoms, preferably 1 to 4 carbon atoms, such as methyl, ethyl, propyl, isopropyl, butyl, isobutyl, sec-butyl, tert-butyl,
- a linear or branched alkenyl radical having 2 to 6 carbon atoms, preferably 2 to 4 carbon atoms, such as vinyl, allyl,
- a linear or branched alkoxy or thioether radical having 1 to 6 carbon atoms, preferably 1 to 4 carbon atoms, such as the methoxy, ethoxy, propoxy, isopropoxy, butoxy radicals, an alkenyloxy radical, preferably an allyloxy radical or a phenoxy radical,
- a cyclohexyl, phenyl, or benzyl radical,
- an acyl group having 2 to 6 carbon atoms,
- a radical of the formula:

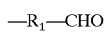

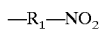

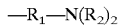

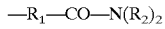

in which formulae $R_1$ represents a valency bond or a divalent linear or branched, saturated or unsaturated divalent hydrocarbon radical having 1 to 6 carbon atoms, such as, for example, methylene, ethylene, propylene, isopropylene, isopropylidene; the radicals $R_2$ are identical or different and represent a hydrogen atom or a linear or branched alkyl radical having 1 to 6 carbon atoms; X symbolises a halogen atom, preferably a chlorine, bromine or fluorine atom.

If n is greater than or equal to 2, two radicals R and the 2 successive atoms of the aromatic ring can be bonded to one another by an alkylene, alkenylene or alkenylidene radical having 2 to 4 carbon atoms to form a saturated, unsaturated or aromatic heterocyclic ring having 5 to 7 carbon atoms. One or more carbon atoms can be replaced by another heteroatom, preferably oxygen or sulphur. The radicals R can thus represent a methylenedioxy or ethylenedioxy radical or a methylene thio radical or ethylene thio radical.

The present invention is applied, more particularly, to aromatic compounds corresponding to the formula (I) in which:

the radical, or radicals, R represents/represent one of the following groups:
- a hydrogen atom
- an OH group,
- a linear or branched alkyl radical having 1 to 6 carbon atoms,
- a linear or branched alkenyl radical having 2 to 6 carbon atoms,
- a linear or branched alkoxy radical having 1 to 6 carbon atoms,
- a —CHO group,
- an acyl group having 2 to 6 carbon atoms,
- a —COOR$_2$ group, where R$_2$ has the meaning given above,
- a —NO$_2$ group.
- a —NH$_2$ group,
- a halogen, preferably fluorine, chlorine, bromine, atom,
- a —CF$_3$ group, n is a number equal to 0, 1, 2 or 3.

Among the compounds of the formula (I), those corresponding to the following formulae are more particularly used:
- a monocyclic or polycyclic, aromatic carbocyclic compound having rings which can form with one another an orthocondensed system corresponding to the formula (Ia):

$$(Ia)$$

in which formula (Ia) m represents a number equal to 0, 1 or 2, and the symbols R, which are identical or different, and n having the meaning given above,
- a compound made up of a chain of two or more monocyclic aromatic carbocyclic rings corresponding to the formula (Ib):

$$(Ib)$$

in which formula (Ib) the symbols R, which are identical or different, and n have the meaning given above, p is a number equal to 0, 1, 2 or 3 and B represents:
- a valency bond
- an alkylene or alkylidene radical having 1 to 4 carbon atoms, preferably a methylene or isopropylidene radical,
- one of the following groups:

—O—, —CO—, —COO—, —OCOO—
—S—, —SO—, —SO$_2$—,

—N—,  —CO—N—,
  |            |
  R$_0$         R$_0$ in which formulae, R$_o$ represents a hydrogen atom or an alkyl radical having 1 to 4 carbon atoms, a cyclohexyl or phenyl radical.

The compounds of the formula (I) which are preferably used correspond to the formulae (Ia) and (Ib) in which:
- R represents a hydrogen atom, a hydroxyl group, a thiol group, a —CHO group, a —NO$_2$ group, a —NH$_2$ group, a linear or branched alkyl or alkoxy radical having 1 to 6 carbon atoms, preferably 1 to 4 carbon atoms, or a halogen atom,
- B symbolizes a valency bond, an alkylene or alkylidene radical having 1 to 4 carbon atoms or an oxygen atom,
- m is equal to 0 or 1,
- n is equal to 0, 1 or 2
- p is equal to 0 or 1.

Still more preferably, the compounds of the formula (I) in which R represents a hydrogen atom, a hydroxyl group, a methyl radical, a methoxy radical or a halogen atom are chosen.

By way of illustration of compounds corresponding to the formula (I), more particular mention may be made of:
- halogenated or non-halogenated aromatic compounds, such as benzene, toluene, chlorobenzene, iodobenzene, the dichlorobenzenes, the trichlorobenzenes, fluorobenzene, the difluorobenzenes, the chlorofluorobenzenes, the chlorotoluenes, the fluorotoluenes, bromobenzene, the dibromobenzenes, the bromofluorobenzenes, the bromochlorobenzenes, trifluoromethylbenzene, trifluoromethoxybenzene, trichloromethylbenzene, trichloromethoxybenzene, trifluoromethylthiobenzene,
- aminated or nitrated aromatic compounds, such as aniline and nitrobenzene,
- phenolic compounds, such as phenol, o-cresol, guaiacol, fluorophenol, α-naphtol, β-naphtol,
- monoethers, such as anisole, ethoxybenzene (phenetole), butoxybenzene, isobutoxybenzene, 2-chloroanisole, 3-chloroanisole, 2-bromoanisole, 3-bromoanisole, 2-methylanisole, 3-methylanisole, 2-ethylanisole, 3-ethylanisole, 2-isopropylanisole, 3-isopropylanisole, 2-propylanisole, 3-propylanisole, 2-allylanisole, 2-butylanisole, 3-butylanisole, 2-tert-butylanisole, 3tert-butylanisole, 2-benzylanisole, 2-cyclohexylanisole, 1-bromo-2-ethoxybenzene, 1-bromo-3-ethoxybenzene, 1-chloro-2ethoxybenzene, 1-chloro-3-ethoxybenzene, 1-ethoxy-2-ethylbenzene, 1-ethoxy-3-ethylbenzene, 2,3-dimethylanisole, 2,5-dimethylanisole, 1-methoxynaphthalene, 2-methoxynaphthalene,
- diethers, such as veratrole, 1,3-dimethoxybenzene, 1,2-diethoxybenzene, 1,3-diethoxybenzene, 1,2-dipropoxybenzene, 1,3-dipropoxybenzene, 1,2-methylenedioxybenzene, 1,2-ethylenedioxybenzene,
- triethers, such as 1,2,3-trimethoxybenzene, 1,3,5-trimethoxybenzene, 1,3,5-triethoxybenzene,
- thioethers, such as thioanisole, o-thiocresol, m-thiocresol, p-thiocresol, 2-thioethylnaphtalene, S-phenylthioacetate, 3-(methylmercapto)aniline, phenylthiopropionate.

The compounds to which the process according to the invention applies in a more particularly interesting manner are benzene, toluene, the mono- and dichlorobenzenes, fluorobenzene, iodobenzene, phenol, fluorophenol, anisole, veratrole, 1 -methoxynaphthalene, 2-methoxynaphthalene.

As for the acylating reagent, use is made of carboxylic acids and their derivatives, halides or anhydrides, preferably anhydrides.

As regards the sulphonylating agent, use is made, more particularly, of the sulphonyl- or aminosulphonyl- halides or anhydrides.

As regards the acylating or sulphonylating reagents, these more particularly correspond to the following formulae:

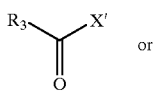

(II)

or

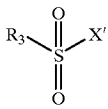

(III)

in which formulae (II) or (III):
$R_3$ represents:
a saturated or unsaturated, linear or branched aliphatic radical having 1 to 24 carbon atoms; a saturated, unsaturated or aromatic, monocyclic or polycyclic cycloaliphatic radical having 4 to 12 carbon atoms; a saturated or unsaturated, linear or branched aliphatic radical which carries a cyclic substituent,
X' represents:
a halogen atom, preferably a chlorine or bromine atom,
in formula (II):
X' represents a —O—CO—$R_4$ radical, where $R_4$ is identical to or different from $R_3$ and has the same meaning as $R_3$.
in formula (III):
X' represents a —O—$SO_2$—$R_4$ being identical to or different from $R_3$, having the same meaning as $R_3$,
$R_3$ represents:
a $R_5$—O— alkoxy radical with $R_5$ having the same meaning as $R_3$,
a $(R_6)$ $(R_7)$ —N—amino group with $R_6$ which is identical to or different from $R_7$ having the same meaning as $R_3$.

Cyclic substituent is understood preferably as meaning a carbocyclic ring which is saturated, unsaturated or aromatic, preferably cycloaliphatic or aromatic, in particular cycloaliphatic containing 6 carbon atoms in the ring or benzenic.

More particularly, $R_3$ represents a linear or branched alkyl radical having 1 to 12 carbon atoms, preferably 1 to 6 carbon atoms; it being possible for the hydrocarbon chain to be optionally interrupted by a heteroatom (e.g. oxygen), by a functional group (e.g. —CO—) and/or to carry a substituent (e.g. a halogen or a $CF_3$ group).

$R_3$ preferably represents an alkyl radical having 1 to 4 carbon atoms, such as methyl, ethyl, propyl, isopropyl, butyl, isobutyl, sec-butyl, tert-butyl.

The radical $R_3$ also preferably represents a phenyl radical, which can be optionally substituted. It is necessary that this radical is more deactivated than the aromatic compound, since otherwise acylation of the acylating agent itself would be promoted.

As more particular examples of substituents, the following may be mentioned more especially:
a linear or branched alkyl radical having 1 to 6 carbon atoms, preferably 1 to 4 carbon atoms, such as methyl, ethyl, propyl, isopropyl, butyl, isobutyl, sec-butyl, tert-butyl,
a linear or branched alkoxy radical having 1 to 6 carbon atoms, preferably 1 to 4 carbon atoms, such as the methoxy, ethoxy, propoxy, isopropoxy, butoxy, isobutoxy, sec-butoxy, tert-butoxy radicals,
a hydroxyl group,
a halogen atom, preferably a fluorine, chlorine or bromine atom.

The preferred acylating agents correspond to the formula (II) in which X' represents a chlorine atom and $R_3$ represents a methyl or ethyl radical.

If the acylating agent is an acid anhydride, the preferred compounds correspond to the formula (II) in which $R_3$ and R4 are identical and represent an alkyl radical having 1 to 4 carbon atoms.

As far as the sulphonylating agents are concerned, they preferably correspond to formula (III) in which X' represents a chlorine atom or a —O—$SO_2$—R4 radical in which R4 represents an alkyl radical with 1 to 4 carbon atoms and $R_3$ represents a phenyl or naphtyl radical or a $R_5$—O—radical or $(R_6)(R_7)$—N—radical in which $R_5$, $R_6$ and $R_7$ represent a linear or branched alkyl radical with 1 to 4 carbon atoms.

By way of illustration of acylating agents corresponding to the formula (II) there may be mentioned more particularly:
acetyl chloride,
acetyl bromide,
monochloroacetyl chloride,
dichloroacetyl chloride,
propanoyl chloride,
isobutanoyl chloride,
pivaloyl chloride,
stearoyl chloride,
crotonyl chloride,
benzoyl chloride,
the chlorobenzoyl chlorides,
p-nitrobenzoyl chloride,
o-nitrobenzoyl chloride,
the methoxybenzoyl chlorides,
the naphthoyl chlorides,
acetic anhydride,
isobutyric anhydride,
trifluoroacetic anhydride,
benzoic anhydride.

The following examples can be given, inter alia, for sulphonylating agents corresponding to general formula (II):
benzenesulphonyl chloride,
p-chlorobenzenesulphonyl chloride,
fluorobenzenesulphonyl chloride,
nitrobenzenesulphonyl chloride,
methoxybenzenesulphonyl chloride,
tosyle chloride,
dimethylsulphamoyl chloride,
methoxysulphonyl chloride,
benzenesulphonic anhydride,
p-toluenesulphonic anhydride.

According to the process of the invention, the acylation or sulphonylation reaction of an aromatic compound is carried out in the presence of a catalyst under microwave irradiation.

An essential characteristic of the invention comprises reaction of the substrate and the acylating or sulphonylating agent under the action of microwaves.

The exposure of the reaction mixture to the action of microwaves allows activation of the mixture in a manner comparable to heat within the latter. It has been found that this activation produces a remarkable improvement in the reaction kinetics.

The reaction time can vary according to the power applied, notably from 30 s to 1 h, in particular from 1 to 30 min.

It is difficult to define a temperature of a mixture during exposure to microwaves. However, it can be said that the temperature on the surface of the reaction mixture is advantageously between 60° C. and 350° C., preferably between 100° C. and 150° C.

The exposure of the reaction mixture to microwaves is advantageously such that the mixture is subject to radiation with an energy at least equal to 10 W, preferably between 30 and 300 W.

If one of the molecules to be irradiated is volatile it is recommended that the incident energy is advantageously between 30 and 100 W.

The microwave frequency which can be used is between about 100 MHz and about 10 GHz, advantageously between about 300 MHz and 3 GHz.

The microwave wavelength which can be used is generally between 10 cm and 1 m in air.

The exposure to microwaves can be carried out in a continuous, discontinuous, or sequential manner, with sequences of, for example, 15 s to 1 min.

The catalyst involved in the process of the invention is a catalyst of the Friedel-Crafts type.

A first class of catalyst which is suitable for the invention are the Lewis acids.

As examples of organic salts there may be mentioned, in particular, acetate, propionate, benzoate, methanesulphonate, trifluoromethanesulphonate of metallic or metalloid elements of groups (IIIa), (IVa), (VIII), (IIb), (IVb), (Vb), (Vb) and (VIb) of the periodic table of elements.

As regards the inorganic salts, there may be mentioned chloride, bromide, iodide, sulphate, oxide and analogous products of metallic or metalloid elements of groups (IVa), (VIII), (IIb), (IIIb), (IVb), (Vb) and (VIb) of the periodic table of elements.

In the present text, reference is made below to the periodic table of elements published in the Bulletin de la Société Chimique de France, no. 1 (1966).

The salts used in the process of the invention are more particularly those of elements of group (IIIa) of the periodic table, preferably scandium, yttrium and the lanthanides; of group (IVa), preferably titanium, zirconium; of group (VIII), preferably iron; of group (IIb), preferably zinc; of group (IIIb), preferably boron, aluminium, gallium, indium; of group (IVb), preferably tin; of group (Vb), preferably bismuth; of group (VIb), preferably tellerium.

Among the inorganic salts there may be mentioned the metal halides, and preferably zirconium chloride, ferric chloride, zinc chloride, aluminium chloride, aluminium bromide, gallium chloride, indium chloride, stannic chloride, bismuth chloride, boron trifluoride; ferrous oxide, ferric oxide, gallium oxide.

It is possible to generate a halide in situ and thus to use any compound of the above-mentioned elements as long as it is combined with a source of halogen.

The metal or that in any form can thus be used. They can be introduced in the form of the metal or oxide or in saline form, as a simple or double, mineral or organic salt.

As mentioned hereinabove, the above-mentioned elements can be introduced in the form of a metal or in the form of an oxide or a hydroxide. It is possible to use a mineral salt, preferably nitrate, sulphate, oxysulphate, halide, oxyhalide, silicate, carbonate, oxalate, or an organic salt, preferably acetylacetonate; alcoholate, and still more preferably methylate or ethylate; carboxylate, and still more preferably acetate.

As regards the source of halogen, any compound which is capable of introducing halogen ions enabling the metal or metalloid halide to be generated in situ can be used.

As examples of sources of halogen there may be used halogen in molecular form; any halide of a mineral or organic acid, and more particularly of aliphatic carboxylic acids; any mineral or organic metal or metalloid salt which is capable of generating a halogenated form.

As more specific examples there may be mentioned, inter alia, chlorine or bromine; hydrochloric acid, hydrobromic acid; acetyl chloride; silicon chloride $SiCl_4$, halogenosilanes, such as $Me_3SiCl$, $Me_2SiCl_2$, $MeSiCl_3$, $PhMe_2SiCl$, phosphorus chloride $PCl_3$, sulphur chloride $SC_2$.

As regards the organic salts, the salts of rare earths and/or bismuth with trifluoromethanesulphonic acid, generally called "triflic acid" are preferably used. "Rare earth" is understood as meaning the lanthanides having an atomic number from 57 to 71 and yttrium, as well as scandium.

As regards the triflate of a rare earth used as the catalyst, this is more particularly that of a rare earth chosen from lanthanides, yttrium, scandium and their mixtures, preferably lanthanides such as lanthanum, cerium, praseodymium, neodymium, samarium, europium, gadolinium, terbium, dysprosium, holmium, erbium, thulium, ytterbium and lutetium and their mixtures.

The following rare earths are more particularly envisaged in the process of the invention: lanthanum, ytterbium, lutetium and their mixtures.

The triflates of rare earths are known products which are described in literature, in particular in U.S. Pat. No. 3,615, 169. They are generally obtained by reaction of the rare earth oxide and trifluoromethanesulphonic acid.

The salts of bismuth with triflic acid described in the patent application PCT/FR96/01488 can also be used in the process of the invention.

Another class of catalysts which is suitable for the invention are the Brönsted acids, and more particular mention may be made of sulphuric acid, hydrofluoric acid, hydrochloric acid, the phosphoric acids and the polyphosphoric acids, the sulphonic acids, and, in particular, trifluoromethanesulphonic acid, perfluorosulphonic acid, trifluorosulphonic acid.

A bulk catalyst as mentioned above can be used in the process of the invention.

According to another use variant, a catalyst in supported form can be used. To this end, the support can be chosen from the oxides of metals, such as the oxides of aluminium, silicon and/or zirconium, clays, and, more particularly, kaolin, talc or montmorillonite, or also from charcoals which are optionally activated by a well-known treatment with nitric acid, acetylene black, or resins.

The support can be in any form, for example a powder, beads, granules, extrudates . . .

In the description, "catalyst" will mean both the bulk catalyst and the supported catalyst prepared according to techniques known to the person skilled in the art.

The content of active phase in the catalyst represents 5 to 100% of the weight of the catalyst.

According to the process of the invention, the reaction between the aromatic compound and the acylating or sulphonating agent is carried out in a liquid phase in the presence or absence of an organic solvent; it being possible for one of the reagents to be used as the reaction solvent.

A preferred variant of the process of the invention comprises carrying out the reaction in an organic solvent.

Several requirements govern the choice of solvent.

The solvent is chosen such that it does not absorb microwaves.

It should be inert under the conditions of the invention and have a boiling point higher than the reaction temperature.

It is desirable for the solvent to be anhydrous.

An aprotic organic solvent of low polarity is preferably used.

As examples of solvents which are suitable for the present invention particular mention may be made of halogenated or non-halogenated aliphatic or aromatic hydrocarbons.

By way of examples of aliphatic hydrocarbons more particular mention may be made of paraffins, such as, in particular, hexane, heptane, octane, nonane, decane, undecane, dodecane, tetradecane or cyclohexane, and the aromatic hydrocarbons, and, more particularly, the aromatic hydrocarbons such as, in particular, benzene, toluene, the xylenes, cumene, petroleum cuts made up of a mixture of alkylbenzenes, in particular the cuts of the Solvesso® type.

As regards the aliphatic or aromatic halogenated hydrocarbons, more particular mention may be made of the perchlorinated hydrocarbons, such as, in particular, tetrachloromethane, tetrachloroethylene, hexachloroethane; the partly chlorinated hydrocarbons, such as dichloromethane, chloroform, 1,2-dichloroethane, 1,1,1-trichloroethane, 1,1,2,2-tetrachloroethane, pentachloroethane, trichloroethylene, 1-chlorobutane, 1,2-dichlorobutane; monochlorobenzene, 1,2-dichlorobenzene, 1,3-dichlorobenzene, 1,4dichlorobenzene, 1,2,4-trichlorobenzene or mixtures of various chlorobenzenes; bromoform, bromoethane or 1,2-dibromoethane; monobromobenzene or mixtures of monobromobenzene with one or more dibromobenzenes; 1-bromonaphthalene.

A mixture of organic solvents can also be used.

A halogenated or non-halogenated heavy hydrocarbon, that is to say having a boiling point of at least 150° C., is preferably used.

The preferred solvents are: o- and m-dichlorobenzene.

In a first stage of the process of the invention, the acylation or sulphonylation of the aromatic compound is carried out. In a following stage, the hydrolysis of the reaction mass obtained is carried out.

The ratio between the number of moles of aromatic compound and the number of moles of acylating or sulphonylating agent can vary, since the substrate can serve as the reaction solvent. The ratio can thus range from 0.1 to 10, preferably between 1.0 and 4.0.

The amount of catalyst used is determined such that the ratio between the number of moles of catalyst and the number of moles of acylating agent or sulphonylating agent is less than 1.0, and preferably varies between 0.001 and 0.8, and still more preferably between 0.02 and 0.2.

As regards the amount of organic solvent used, this is generally chosen such that the ratio between the number of moles of organic solvent and the number of moles of aromatic compound preferably varies between 0 and 100, and still more preferably between 0 and 50.

The temperature at which the acylation or sulphonylation reaction is carried out depends on the power of the microwave radiation.

Generally, the reaction is carried out under atmospheric pressure, but lower or higher pressures may also be appropriate.

From a practical point of view, there are no restrictions regarding the employment of the reagents. They can be introduced in any order.

After the reagents have been brought into contact, the reaction mixture is subjected to a microwave field.

Microwaves can be applied to the reaction mixture by any means known per se.

Advantageously, the device for application of microwaves is in the form of a cavity (reactor) containing the reaction medium. Internal elements which have a highly dissipating effect under microwave radiation and transmit energy to the reaction medium can also be located inside the reactor.

The geometry of the device will advantageously be defined as a function of the characteristics of dissipation of energy through the reaction mixture.

Preferably, a single wave mode will be excited for better control of the dissipation of energy. Reactors designed for continuous processes, the simple (most often cylindrical) geometry of which is suitable for monomodal transmission of waves, will thus be preferred. These continuous reactors can function with recycling of the reaction mixture.

The application can be, in particular, in the form of a tubular reactor located in parallel with a radiating slot wave guide.

However, reactors of the "batch" type for discontinuous processes can also be used to expose the reaction medium to monomodal microwaves. The thermal homogeneity of the reaction mixture is advantageously ensured by rotating the reactor and/or by stirring the mixture in the opposite direction with a glass blade stirrer.

The exposure to microwaves may possibly also be coupled with a conventional heating method.

After the irradiation, in a following stage of the process of the invention, a hydrolysis treatment is carried out on the reaction mass obtained.

The amount of water used may vary very widely. The ratio between the number of moles of water and the number of moles of aromatic compound can vary between 10 and 100, and preferably between 20 and 30.

To this end, a preferred embodiment of this operation comprises adding the reaction mass to a base of water brought to a temperature of between 0° C. and 100° C., preferably between 15° C. and 30° C.

One variant of the invention comprises replacing the water by a basic solution, generally of soda, sodium carbonate or sodium bicarbonate having a concentration of 5 to 20% by weight.

The catalyst is separated off, preferably by filtration. After drying, the catalyst can be recycled.

At the end of the reaction, the desired product, that is to say the aromatic ketone or sulphone, is obtained in the organic phase.

The aqueous and organic phases are separated.

The organic phase is washed with water once or several times, preferably twice.

The aqueous and organic phases are separated.

The aromatic ketone or aromatic sulphone is then recovered from the organic phase by known techniques, by removal of the organic solvent by distillation or by crystallization.

Another variant of the invention comprises recovering the organic ketone directly, by distillation of the organic phase containing this and the catalyst.

According to the process of the invention, an aromatic ketone which can be represented by the formula (IV) is obtained:

in which formula (IV) A, R, $R_3$ and n have the meaning given above.

According to the process of the invention, it is also possible to obtain an aromatic sulphone corresponding to formula (V):

in which formula (V), A, R, $R_3$ and n have the meaning given hereinabove.

The examples which follow illustrate the invention, but without limiting it.

In the examples, the yields mentioned correspond to the following definition:

Yield = number of moles of aromatic ketone formed % number of moles of minority reactant "Minority reactant" is understood as meaning either the aromatic substrate or the acylating agent or sulphonylating agent depending on the relative amounts of each introduced.

EXAMPLES

In the examples, the reactions are carried out in a Synthewave® 402-230V oven marketed by the company Prolabo, under monomodal microwave irradiation ($TE_{10}$) at a frequency of 2.45 GHz.

The flask used is that provided by the company Prolabo, either of quartz or of borosilicate glass.

The oven is equipped with a system for rotating the flask, and a cooling agent or a cooling finger containing a liquid at a low temperature, depending on the boiling point of the products to be condensed, and a drying tube (calcium chloride, for example).

The reactions are carried out under atmospheric pressure.

The reaction mixture is heated under microwave irradiation at a given power, either continuously or discontinuously. The power stated in the text and in the tables is the incident power supplied by the magnetron and indicated by the Synthewave wattmeter. The comparison experiments on the same group of examples were carried out with the same amounts of reactants. The power of the radiation absorbed per unit volume of reaction medium could be evaluated for each group of examples.

After the reaction mass has been cooled, this is treated with an aqueous 10% by weight solution of sodium hydroxide.

The organic phase is extracted with the aid of a suitable solvent (such as, for example, ethyl ether), separated off from the aqueous phase and dried over sodium sulphate.

After evaporation of the solvent, the reaction product is analysed by gas phase chromatography GC/mass spectrometry MS (Hewlett-Packard GC 5890-MS 5989) and by nuclear magnetic resonance NMR (Bruker AC 80 and AM 300).

The purifications are carried out by chromatography over a silica gel column.

It should be noted that the temperatures stated in the examples are evaluated with the aid of an infra-red pyrometer incorporated in the apparatus and coupled to a recorder, which enables the changes in temperature under microwave irradiation to be displayed.

The temperatures measured are thus surface temperatures.

The temperatures at the centre of the reaction mixture measured with the aid of a thermocouple immediately after the end of an irradiation are close to those as long as the reaction mixture is agitated. Otherwise, the temperature in the centre may exceed the temperature displayed by the infrared thermometer by 10 to 30° C.

Examples 1 to 11

A flask equipped with a cooling agent and a $CaCl_2$ tube is charged with:

4.32 g (40 mmol) anisole, 1.40 g (10 mmol) benzoyl chloride, 10 mol %, expressed with respect to benzoyl chloride, of a catalyst, the nature of which is stated in the following table I.

The reaction mixture is heated under microwave irradiation for 1 minute with of 300 W.

At the end of the reaction, the temperature of the reaction mixture is measured aid of a thermocouple and recorded in the following table.

After cooling, the reaction mass is hydrolysed with a 10% solution of sodium hydroxide. The organic phase is extracted with ether, separated off from the aqueous phase and dried over sodium sulphate.

The solvent is evaporated off and the products are analysed by GC, GC/MS and NMR.

The yields of methoxybenzophenone are expressed with respect to an internal reference (dodecane) and are shown in relation to the minority reactant (PhCOCl).

TABLE I

| Ex. no. | Nature of the catalyst | Temperature at the end of the reaction (° C.) | Yield (%) | Isomers (%) para/ortho |
|---|---|---|---|---|
| 1 | $FeCl_3$ | 160 | 86 | 94/6 |
| 2 | $AlCl_3$ | 157 | 85 | 93/7 |
| 3 | $GaCl_3$ | 167 | 87 | 94/6 |
| 4 | $BiCl_3$ | 157 | 70 | 92/8 |
| 5 | $ZrCl_4$ | 153 | 77 | 95/5 |
| 6 | $InCl_3$ | 168 | 76 | 94/6 |
| 7 | $ZnCl_2$ | 142 | 66 | 93/7 |
| 8 | $SnCl_2,2H_2O$ | 147 | 43 | 93/7 |
| 9 | $Fe_2O_3$ | 164 | 78 | 93/7 |
| 10 | $Fe_3O_4$ | 162 | 89 | 93/7 |
| 11 | $Ga_2O_3$ | 164 | 88 | 94/6 |

Examples 12 to 16

Examples 1 to 11 are repeated, except that the flask is charged with:

4.32 g (40 mmol) anisole 1.40 g (10 mmol) benzoyl chloride, 2 mol %, expressed with respect to benzoyl chloride, of a catalyst, the nature of which is stated in the following table II.

TABLE II

| Ex. No. | Nature of the catalyst | Temperature at the end of the reaction (° C.) | Yield (%) | Isomers (%) para/ortho |
|---|---|---|---|---|
| 12 | Ce(OTf)$_3$ | 132 | 12 | 9/91 |
| 13 | Yb(OTf)$_3$ | 133 | 33 | 7/93 |
| 14 | Sc(OTf)$_3$ | 136 | 35 | 8/92 |
| 15 | Sn(OTf)$_3$ | 139 | 44 | 10/90 |
| 16 | Bi(OTf)$_3$ | 143 | 64 | 9/91 |

Examples 17 to 21

The operating method of examples 1 to 11 is followed, except that the nature of the acylating agent and the irradiation conditions are changed.

The molar ratio between the two reactants is indicated in the following table and is such that the total reaction volume is 5 ml.

The maximum temperature observed in the course of the various intervals is measured with the aid of an infrared thermometer.

The yields of aromatic ketone are expressed with respect to the minority reactant. The para-isomer is the majority isomer (96 to 99%) over the ortho-isomer.

TABLE III

| Ex. No. | Molar ratio anisole: acylating agent | Nature of the catalyst | Mol % of the catalyst with respect to anisole | Nature of the acylating agent | Conditions: power; Tmax; irradiation; time; Δt* | Yield (%) |
|---|---|---|---|---|---|---|
| 17 | 1:1 | FeCl$_3$ | 5 | Isobutanoyl chloride | 60 W; 87° C.; 8 × 15 s; 45 s | 77 |
| 18 | 1:2 | FeCl$_3$ | 10 | Acetyl chloride | 60 W; 93° C.; 16 × 15 s; 45 s | 68 |
| 19 | 1:2 | Fe$_3$O$_4$ | 3 | Acetyl chloride | 60 W; 84° C.; 32 × 15 s; 45 s | 40 |
| 20 | 1:2 | Fe$_3$O$_4$ | 3 | Acetyl bromide | 60 W; 87° C.; 32 × 15 s; 45 s | 37 |
| 21 | 1:2 | FeCl$_3$ | 10 | Acetic anhydride | 300 W; 158° C.; 12 × 15 s; 45 s | 90 |

*interval between two successive irradiations.

Examples 22 to 30

A flask equipped with a cooling agent and a ClCl$_2$ tube is charged with:

3.68 g (40 mmol) toluene, 1.40 g (10 mmol) benzoyl chloride, x mol %, expressed in relation to benzoyl chloride, of a catalyst, the nature of which is stated in the following table.

The irradiation conditions are shown in Table IV.

In these examples, the maximum temperature observed is measured by a thermocouple.

After treatment according to example 1, the organic products are analysed by GC/MS and NMR.

The yields of methylbenzophenone are expressed with respect to benzoyl chloride. The para-isomer is the majority isomer (81 to 91%) over the ortho-isomer (8 to 16%) and the meta-isomer (0 to 5%).

TABLE IV

| Ex. No. | Nature of the catalyst | Mol % of the catalyst with respect to the acylating agent | Conditions: power; Tmax; irradiation time; Δt* | Yield (%) |
|---|---|---|---|---|
| 22 | FeCl$_3$ | 10 | 120 W; 118° C.; 1 min; continuous irr. | 36 |
| 23 | FeCl$_3$ | 5 | 300 W; 121° C.; 15 × 20 s; 1 min 40 s | 90 |
| 24 | GaCl$_3$ | 10 | 120 W; 116° C.; 1 min; continuous irr. | 29 |
| 25 | GaCl$_3$ | 10 | 120 W; 125° C.; 10 × 1 min; 1 min | 50 |
| 26 | AlCl$_3$ | 10 | 120 W; 117° C.; 1 min; continuous irr. | 8 |
| 27 | AlCl$_3$ | 10 | 300 W; 119° C.; 15 × 20 s; 40 s | 12 |
| 28 | AlCl$_3$ | 40 | 300 W; 122° C.; 15 × 20 s; 40 s | 43 |
| 29 | ZrCl$_4$ | 10 | 120 W; 111° C.; 1 min; continuous irr. | 11 |
| 30 | ZrCl$_4$ | 10 | 120 W; 117° C.; 10 × 1 min; 30 s | 21 |

*Interval between two successive irradiations.

Example 31

The operating method of examples 22 to 30 is followed, except that the reaction volume is changed (5 ml, as for examples 17 to 21), the same molar ratio (4:1) between the toluene and the benzoyl chloride still being maintained.

The results obtained are as follows:

TABLE V

| Ex. No. | Nature of the catalyst | Mol % of catalyst with respect to the acylating agent | Conditions: power; Tmax; irradiation time; Δt* | Yield (%) |
|---|---|---|---|---|
| 31 | $Fe_3O_4$ | 10 | 300 W; 93° C.; 18 × 20 s; 40 s | 46 |

*Interval between the two successive irradiations.

Examples 32 to 35

In these examples, the activation, under a microwave field, of acylation reactions on a non-activated aromatic substrate such as benzene is demonstrated.

A flask equipped with a cooling agent and a $CaCl_2$ tube is charged with:
- 40 mmol benzene,
- 10 mmol acylating agent,
- x mol %, expressed with respect to the acylating agent, of a catalyst, the nature of which is stated in the following table VI.

The reaction mixture is heated under a microwave field for a period shown in the table.

After treatment according to example 1 (extraction solvent $CH_2Cl_2$) and removal of the benzene, the organic products are analysed by GC, GC/MS and NMR.

The yields of aromatic ketone are expressed in product isolated and are shown in relation to the minority reactant (RCOCl).

In the case of example 33, the molar ratio between the benzene and the benzoyl chloride is only 2:1.

TABLE VI

| Ex. No. | Nature of the catalyst | Mol % of the catalyst with respect to the acylating agent | Nature of the acylating agent | Conditions: power; Tmax; irradiation time; Δt* | Yield (%) |
|---|---|---|---|---|---|
| 32 | $GaCl_3$ | 10 | Benzoyl chloride | 120 W; 96° C.; 10 × 1 min; 1 min | 17 |
| 33 | $FeCl_3$ | 8 | Benzoyl chloride | 300 W; 135° C.; 25 × 15 s; 45 s | 61 |
| 34 | $FeCl_3$ | 8 | 4-Nitrobenzoyl chloride | 300 W; 109° C.; 4 × 1 min; 1 min + 10 × 30 s; 30 s + 12 × 15 s; 45 s | 75 |
| 35 | $FeCl_3$ | 5 | 2-chlorobenzoyl chloride | 300 W; 127° C.; 3 × 1 min; 1 min + 10 × 30 s; 30 s + 12 × 15 s; 45 s | 83 |

*interval between two successive irradiations.
- In examples 34 and 35, three successive irradiation sequences were carried out.

Examples 36 to 38

In these examples, the activation, under a microwave field, of acylation reactions on a deactivated aromatic substrate such as chlorobenzene is demonstrated.

The conditions of examples 32 to 35 are reproduced.

The aromatic substrate is chlorobenzene in all the examples, with a molar ratio with respect to the acylating agent of 1:1 for examples 36 and 37; and of 2:1 for example 38.

The para-isomer of the aromatic ketone obtained is the majority isomer (94 to 99%) over the ortho-isomer.

TABLE VII

| Ex. No. | Nature of the catalyst | Mol % of the catalyst with respect to the acylating agent | Nature of the acylating agent | Conditions: power; Tmax; irradiation time; Δt* | Yield (%) |
|---|---|---|---|---|---|
| 36 | $FeCl_3$ | 10 | Benzoyl chloride | 300 W; 246° C.; 15 × 30 s; 30 s | 62 |
| 37 | $FeCl_3$ | 5 | 4-Nitrobenzoyl chloride | 300 W; 198° C.; 1 × 3 min; 1 min + 8 × 30 s; 30 s + 12 × 15 s; 45 s | 80 |

TABLE VII-continued

| Ex. No. | Nature of the catalyst | Mol % of the catalyst with respect to the acylating agent | Nature of the acylating agent | Conditions: power; Tmax; irradiation time; Δt* | Yield (%) |
|---|---|---|---|---|---|
| 38 | FeCl$_3$ | 5 | 2-chlorobenzoyl chloride | 300 W; 176° C. 1 × 5 min; 1 min + 3 × 1 min; 1 min + 10 × 30 s; 30 s | 85 |

*Interval between two successive irradiations.
- In examples 37 and 38, three successive irradiation sequences were carried out.

Examples 39 to 41

In these examples, the nature of the deactivated aromatic substrate is changed.

The conditions of examples 32 to 35 are reproduced.

The aromatic substrate is fluorobenzene in all the examples.

The para-isomer of the aromatic ketone obtained is the majority isomer (95 to 100%) over the ortho-isomer.

TABLE VIII

| Ex. No. | Nature of the catalyst | Mol % of the catalyst with respect to the acylating agent | Nature of the acylating agent | Conditions: power; Tmax; irradiation time; Δt* | Yield (%) |
|---|---|---|---|---|---|
| 39 | FeCl$_3$ | 10 | Benzoyl chloride | 300 W; 185° C.; 1 × 1 min; 1 min + 2 × 30 s; 30 s + 19 × 15 s; 45 s | 57 |
| 40 | FeCl$_3$ | 10 | 4-Nitro benzoyl chloride | 300 W; 90° C.; 1 × 3 min; 1 min + 2 × 2 min; 1 min + 5 × 1 min; 1 min + 12 × 30 s; 30 s | 54 |
| 41 | FeCl$_3$ | 10 | 2-Chloro benzoyl chloride | 300 W; 118° C.; 1 × 1.5 min; 1 min + 4 × 30 min; 1 min + 22 × 15 s; 1 min | 85 |

*Interval between two successive irradiations.
- In examples 39 to 41, three to four successive irradiation sequences were carried out.

Examples 42 to 44

In these examples, the activation, under a microwave field, of acylation reactions on a highly deactivated aromatic substrate such as 1,3-dichlorobenzene is demonstrated.

A flask equipped with a cooling agent and a CaCl$_2$ tube is charged with:

- 20 mmol 1.3-dichlorobenzene,
- 10 mmol acylating agent,
- x mol %, expressed with respect to the acylating agent, of a catalyst, the nature of which is stated in the following table IX.

The conditions of examples 32 to 35 are then reproduced.

In the case of example 44, the organic phase is analysed by chromatography over a Silicagel Merck 60 column. Elution with pentane allows extraction of 1,3-dichlorobenzene; the expected ketone being eluted with a mixture of pentane/ether (98:2).

TABLE IX

| Ex. No. | Nature of the catalyst | Mol % of the catalyst with respect to the acylating agent | Nature of the acylating agent | Conditions: power; Tmax; irradiation time; Δt* | Yield (%) |
|---|---|---|---|---|---|
| 42 | FeCl$_3$ | 10 | Benzoyl chloride | 300 W;191° C.; 1 × 2 min; 1 min + 13 × 1 min; 1 min | 40 |

TABLE IX-continued

| Ex. No. | Nature of the catalyst | Mol % of the catalyst with respect to the acylating agent | Nature of the acylating agent | Conditions: power; Tmax; irradiation time; Δt* | Yield (%) |
|---|---|---|---|---|---|
| 43 | FeCl₃ | 10 | 4-Nitrobenzoyl chloride | 300 W; 194° C.; 1 × 4 min; 1 min + 4 × 1 min; 1 min + 4 × 30 s; 1 min | 59 |
| 44 | FeCl₃ | 10 | 2-chlorobenzoyl chloride | 300 W; 218° C.; 1 × 4 min; 1 min + 1 × 2 min; 1 min + 3 × 1 min; 1 min + 6 × 30 s; 1 min | 65 |

*Interval between two successive irradiations.
- In examples 42 to 44, two to four successive irradiation sequences were carried out.

Examples 45 and 46

In these examples, the nature of the aromatic substrate used is changed.

A flask equipped with a cooling agent and a CaCl₂ tube is charged with:

20 mmol phenol (10 mmol for 4-fluorophenol), 10 mmol benzoyl chloride, x mol %, expressed with respect to benzoyl chloride, of a catalyst, the nature of which is stated in the following table X.

The conditions of examples 32 to 35 are then reproduced.

The yields of ester formed are expressed in product isolated.

In the case of phenol, treatment of the aqueous phase with a 10% HCl solution followed by an extraction with ether leads, after the organic phase has been separated off, to isolation of the Fries re-arrangement product (2-hydroxybenzophenone: yield 7%).

TABLE X

| Ex. No. | Nature of the aromatic substrate | Nature of the catalyst | Mol % of the catalyst with respect to the acylating agent | Conditions: power; Tmax; irradiation time; Δt* | Yield (%) |
|---|---|---|---|---|---|
| 45 | Phenol | FeCl₃ | 10 | 150 W; 222° C.; 1 × 1 min; 1 min + 20 × 30 s; 1 min | 47 |
| 46 | 4-Fluoro-phenol | FeCl₃ | 10 | 150 W; 161° C.; 2 × 1 min; 1 min + 18 × 30 s; 1 min | 91 |

*Interval between two successive irradiations.
- In examples 45 and 46, two successive irradiation sequences were carried out.

Examples 47 to 49

In these examples, the acetylation of 2-methoxynaphthalene under a microwave field is demonstrated.

A flask equipped with a cooling agent and a CaCl₂ tube is charged with:

1.58 g (10 mmol) 2-methoxynaphthalene, 4.08 g (40 mmol) acetic anhydride, x mol %, expressed with respect to 2-methoxynaphthalene, of a catalyst, the nature of which is stated in the following table XI.

The microwave irradiation conditions are also recorded in the table. The maximum temperature is detected with the aid of a thermocouple.

After cooling, the reaction mass is hydrolysed by a 10% soda solution. The organic phase is extracted with dichloromethane, separated off from the aqueous phase and dried over sodium sulphate, and the solvent is then evaporated off.

The organic products are then extracted three times with pentane and once with ether. The organic phases are combined and concentrated.

The yields of aromatic ketone are calculated by GC.

The percentage of the two isomers obtained is 95% for 1-acetyl-2-methoxynaphthalene and 5% for 2-acetyl-6-methoxynaphthalene, after identification with pure samples of the two products prepared in accordance with S. Pivsa-Art et al., J. Chem. Soc. Perkin Trans 1, (1994) p. 1703.

The results obtained are as follows:

TABLE XI

| Ex. No. | Nature of the catalyst | Mol % of the catalyst with respect to 2-methoxynaphthalene | Conditions: Power; Tmax; Irradiation time; Δt* | Yield (%) |
|---|---|---|---|---|
| 47 | AlCl₃ | 10 | 300 W; 148° C.; 2 × 1 min; 30 s + 4 × 30 s; 30 s | 4 |
| 48 | InCl₃ | 10 | 120 W; 141° C.; 10 × 1 min; 30 s | 56 |
| 49 | FeCl₃ | 10 | 120 W; 155° C.; 6 × 1 min; 30 s | 69 |

* Interval between two successive irradiations.
- In examples 47, two successive irradiation sequences were carried out.

Examples 50 to 62

In these examples, the benzoylation of 2-methoxynaphthalene under a microwave field is demonstrated.

The same operating method of examples 47 to 49 is followed, introducing 1.40 g (10 mmol) benzoyl chloride for these examples.

In the case of example 50, the organic phase is analysed by chromatography over a Silicagel Merck 60 column. Elution with a mixture of pentane/methylene chloride (50/

50) allows extraction in a first period of 1-benzoyl-2-methoxynaphthalene (1), and then 2-benzoyl-6-methoxynaphthalene (2).

The isomers (1) and (2) are identified by GC/MS and NMR with the aid of pure samples prepared in accordance with s. Pivsa-art et al., J. Chem. Soc. Perkin Trans 1, (1994) p. 1703.

TABLE XII

| Ex. No. | Nature of the catalyst | Mol % of the catalyst with respect to the acylating agent | Conditions: Power; Tmax; Irradiation time; Δt* | Yield (%) | % isomers 1/2 |
| --- | --- | --- | --- | --- | --- |
| 50 | FeCl$_3$ | 5 | 300 W; 308° C. 3 min | 63 | 24/76 |
| 51 | InCl$_3$ | 5 | 300 W; 330° C. 3 min | 33 | 13/87 |
| 52 | AlCl$_3$ | 10 | 300 W; 306° C. 3 min | 34 | 33/67 |

*Interval between two successive irradiations.

Examples 53 to 55

In these examples, the possibility of carrying out the acylation reaction in a of the alkane type, which is known not to absorb microwave energy, is demonstrated.

Example 53

The benzoylation of anisole is carried out in nonane (b.p. 151° C.)

A flask equipped with a cooling agent and a CaCl$_2$ tube is charged with:
10 mmol anisole,
10 mmol benzoyl chloride,
10 mol % (1 mmol) FeCl$_3$,
40 mmol nonane.

The microwave irradiation conditions (300 W; 1 min) and the treatment after the reaction which are described in examples 1 to 11 (table I) are reproduced.

The final temperature after irradiation is 142° C.

The yield of methoxybenzophenone is 53% (para-ortho =94/6).

Example 54

The benzoylation of anisole is carried out in undecane (b.p. 196° C.) under the same conditions as above (example 53).

The final temperature after irradiation is 169° C.

The yield of methoxybenzophenone is 83% (para/ortho =96/4).

Example 55

The benzoylation of toluene is carried out in undecane.

A flask equipped with a cooling agent and a CaCl$_2$ tube is charged with:
10 mmol toluene,
10 mmol benzoyl chloride,
10 mol % (1 mmol) FeCl$_3$,
40 mmol undecane.

The microwave irradiation conditions (300 W; 1 min) and the treatment after the reaction are identical to those of examples 53 and 54.

The final temperature after irradiation is 150° C.

The yield of methylbenzophenone is 24% (para/ortho/meta: 82/14/4).

Examples 56 and 57

In these examples, the possibility of carrying out the acylation reaction on an activated aromatic (anisole) in the presence of an aromatic which is not particularly activated or is deactivated and thus serves as the solvent is demonstrated.

Example 56

The benzoylation of anisole is carried out in toluene.

A flask equipped with a cooling agent and a CaCl$_2$ tube is charged with:
20 mmol anisole,
20 mmol toluene,
10 mmol benzoyl chloride,
1 FeCl$_3$.

The microwave irradiation conditions (300 W; 1 min) and the treatment after the reaction which are described in examples 53 and 54 are reproduced.

The final temperature after irradiation is 128° C.

The yield of methoxybenzophenone (para/ortho =94/6) is 90% with respect to benzoyl chloride.

Example 57

The benzoylation of anisole is carried out in o-dichlorobenzene.

A flask equipped with a cooling agent and a CaCl$_2$ tube is charged with:
20 mmol anisole,
20 mmol o-dichlorobenzene,
10 mmol benzoyl chloride,
1 mmol FeCl$_3$.

The microwave irradiation conditions (300 W; 1 min) and the treatment after the reaction which are described in example 55 are reproduced.

The final temperature after the irradiation is 158° C.

The yield of methoxybenzophenone (para/ortho =95/5) is 93% with respect to benzoyl chloride.

In the following examples 58 to 70, the sulphonylation reaction of various aromatic compounds is carried out in accordance with the process of the invention.

The yields given correspond to the following definition:

Yield = number of moles of aromatic sulphone formed / number of moles of sulphonylating agent introduced

Example 58

A quartz flask equipped with a cooling agent and a CaCl$_2$ tube is charged with:
3.69 g (40 mmol) toluene,
3.53 g (20 mmol) benzenesulphonyl chloride,
162 mg (1 mmol), i.e. 5 mol % with respect to the benzenesulphonyl chloride, of anhydrous ferric chloride.

A maximum reference temperature of 110° C. is programmed using the S402 software for the apparatus.

The reaction mixture is heated under microwave irradiation for 5 minutes.

After cooling, the reaction mass is hydrolysed by a 10% by weight solution of sodium hydroxide.

The organic phase is extracted using dichloromethane, dried on sodium sulphate and concentrated at reduced pressure (removal of the excess dichloromethane and toluene).

The solid phase obtained is washed with pentane and treated under reduced pressure at ambient temperature.

The yield of isolated methyldiphenylsulphone in relation to the minority reactant (PhSO$_2$Cl) is 98%.

The isomers are calculated by CG: ortho/meta/para: 38/9/53.

CG/MS [m/z (relative intensity peaks greater than 20%)].
2-methyldiphenylsulphone: 232 (M$^+$, 31), 214 (53), 166 (94), 137 (43), 91 (48), 77 (100), 65 (89);
3-methyldiphenylsulphone: 232 (M$^+$, 42), 139 (51), 125 (100), 91 (37), 77 (49), 65 (48);
4-methyldiphenylsulphone: 232 (M$^+$, 68), 139 (96), 125 (71), 107 (100), 91 (56), 79 (26), 77 (84), 65 (60).

NMR ($^1$H, CDCl$_3$): δ 2.36 (singulet, para-Me), 2,42 (singulet, ortho-Me), 7.10–8.30 (mass of aromatic protons).

Examples 59 to 64

In these examples, the operating method of Example 58 is reproduced.

The irradiation is performed at the maximum temperature indicated in Table XIII.

In example 62, p-chlorodiphenylsulphone is formed (5%).

TABLE XIII

| Ex. No. | Nature of the catalyst | Nature of the sulphonylating agent | Conditions: Power; Tmax; Irradiation time | Yield (%) and isomer ratio |
|---|---|---|---|---|
| 59 | benzene | benzenesulphonyl chloride | 100 W; 78° C. 20 min | 39 |
| 60 | fluoro-benzene | benzenesulphonyl chloride | 100 W; 105° C. 20 min | 73 o/m/p = 2/0/98 |
| 61 | chloro-benzene | p-chlorobenzene-sulphonyl chloride | 100 W: 144° C. 20 min | 95 o/m/p = 7/0/97 |
| 62 | iodo-benzene | p-chlorobenzene-sulphonyl chloride | 120 W; 180° C. 20 min | 72 o/m/p = 3/0/97 |
| 63 | toluene | tosyl chloride | 120 W; 110° C. 5 min | 85 o/m/p = 6/3/91 |
| 64 | toluene | p-toluenesulphonic anhydride | 120 W; 110° C. 10 min | 76 o/m/p = 5/2/93 |

Example 65

A quartz flask equipped with a cooling agent and a CaCl$_2$ tube is charged with:

4.50 g (40 mmol) of chlorobenzene, 3.53 g (20 mmol) of benzenesulphonyl chloride, 162 mg (1 mmol), i.e. 5 mol % in relation to the benzenesulphonyl chloride, anhydrous ferric chloride.

Microwave irradiation is carried out continuously, for 4 minutes, with an incident power of 300 W.

The temperature reached by the reaction medium is 202° C.

The reaction medium is treated as in example 58.

The yield of chlorodiphenylsulphone is 74% in relation to the benzenesulphonyl chloride.

The isomers are calculated by CG:
The ortho/para ratio is 2/98.
The melting point is 95° C.
CG/MS [m/z (%) of 4-chlorodiphenylsulphone: 252 (M$^+$, 23), 159 (40), 125 (100), 111 (21), 97 (24), 77 (71), 75 (34).

TABLE XIV

| Ex. No. | Nature of aromatic compound | Nature of sulphonylating agent | Conditions: Power: T max Irradiation Time | Yield (%) and isomer ratio |
|---|---|---|---|---|
| 65 | Chlorobenzene | Benzenefulfonyl Chloride | 300 W; 202° C. 4 min | 74 o/m/p = 2/0/98 |

Examples 66 to 68

The operating method of Example 65 is reproduced. Microwave irradiation is continued at the power stated. In example 67, 5% diphenylsulphone is formed.

TABLE XV

| Ex. No. | Nature of the aromatic compound | Nature of the sulphonylating agent | Conditions: Power: Tmax Irradiation Time | Yield (%) and Isomer ratio |
|---|---|---|---|---|
| 66 | anisole | benzenesulphonyl chloride | 300 W; 248° C. 1 min | 91 o/m/p = 45/0/55 |
| 67 | iodobenzene | benzenesulphonyl chloride | 300 W; 197° C. 2 min | 90 |
| 68 | iodobenzene | p-chlorobenzene-sulphonyl chloride | 300 W; 220° C. 4 min | 82 o/m/p = 1/0/99 |

Example 69

The reaction is carried out as in example 65, except that sequential irradiation is carried out 6 times 15 s, with intervals of 45 s without irradiation.

TABLE XVI

| Ex. No. | Nature of the aromatic compound | Nature of the sulphonylating agent | Conditions: Power: Tmax Irradiation Time | Yield (%) and Isomer ratio |
|---|---|---|---|---|
| 69 | Benzene | Benzenesulphonyl chloride | 300 W; 160° C. 6 × 15 s; 45 s | 88 |

Example 70

The reaction is carried out as in example 65, except that anisole and dimethylsulfamoyl chloride are used.

TABLE XVI

| Ex. No. | Nature of aromatic compound | Nature of sulphonylating agent | Conditions: Power: Tmax Irradiation Time | Yield (%) and isomer ratio |
|---|---|---|---|---|
| 70 | anisole | dimethyl-sulphamoyl chloride | 300 W; 270° C. 1 min | 60 o/m/p = 42/2/56 |

What is claimed is:

1. A process for the acylation or sulphonylation of an aromatic compound comprising reacting at least one aromatic compound with an acylating or sulphonylating agent in the presence of a Friedel-Crafts catalyst, wherein the acylation or sulphonylation reaction is carried out in liquid phase under microwave irradiation.

2. A process according to claim 1, wherein the aromatic compound corresponds to formula (I):

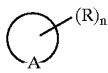
(I)

wherein:
A symbolises the residue of a ring which forms all or part of a monocyclic or polycyclic aromatic carbocyclic or heterocyclic system, said cyclic residue being able to carry a radical R which represents a hydrogen atom or one or more substituents which are identical or different, n represents the number of substituents on the ring.

3. A process according to claim 2, wherein the aromatic compound corresponds to formula (I) in which the residue A which is optionally substituted represents the residue:
1) of a monocyclic or polycyclic aromatic carbocyclic compound,
2) of a monocyclic or polycyclic aromatic heterocyclic compound, or
3) of a compound constituted by a chain of rings, as defined in paragraph and/or 2 bonded to one another:
by a valency bond,
by an alkylene or alkylidene radical with 1 to 4 carbon atoms,
by one of the following groups:

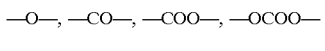

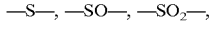

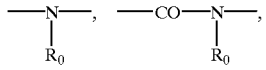

in which formulae, $R_0$ represents a hydrogen atom or an alkyl radical having 1 to 4 carbon atoms, a cyclohexyl or phenyl radical.

4. A process according to claim 2, wherein the aromatic compound corresponds to formula (1) in which the radical(s) represents/represent one of the following groups:
a hydrogen atom,
a linear or branched alkyl radical having 1 to 6 carbon atoms,
a linear or branched alkenyl radical having 2 to 6 carbon atoms,
a linear or branched alkoxy or thioether radical having 1 to 6 carbon atoms,
a cyclohexyl, phenyl, or benzyl radical,
an acyl group having 2 to 6 carbon atoms,
a radical of the formula:

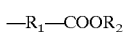

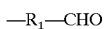

—$R_1$—N($R_2$)$_2$

—$R_1$—CO—N($R_2$)$_2$

—$R_1$—X

—$R_1$—CF$_3$ in which formulae $R_1$ represents a valency bond or a divalent linear or branched, saturated or unsaturated hydrocarbon radical having 1 to 6 carbon atoms; the radicals $R_2$ are identical or different and represent a hydrogen atom or a linear or branched alkyl radical having 1 to 6 carbon atoms; X symbolises a halogen atom.

5. A process according to claim 2, wherein the aromatic compound corresponds to formula (I) in which n is greater than or equal to 2, two radicals R and the 2 successive atoms of the aromatic ring can be bonded to one another by an alkylene, alkenylene or alkenylidene radical having 2 to 4 carbon atoms to form a saturated, unsaturated or aromatic heterocyclic ring having 5 to 7 carbon atoms: one or more carbon atoms being able to be replaced by another heteroatom.

6. A process according to claim 2, wherein the aromatic compound corresponds to formula (I) in which:
the radical, or radicals, R represents/represent one of the following groups:
a hydrogen atom,
an OH group,
linear or branched alkyl radical having 1 to 6 carbon atoms,
linear or branched alkenyl radical having 2 to 6 carbon atoms,
linear or branched alkoxy radical having 1 to 6 carbon atoms,
a —CHO group,
an acyl group having 2 to 6 carbon atoms,
a —COOR$_2$ group, where $R_2$ has the meaning given above,
a —NO$_2$ group,
a —NH$_2$ group,
a halogen atom,
a —CF$_3$ group,
n is a number equal to 0, 1, 2 or 3.

7. A process according to claim 2, wherein the aromatic compound corresponding to formula (I) is a monocyclic or polycyclic, aromatic carbocyclic compound having rings which can form with one another an orthocondensed system corresponding to the formula (Ia):

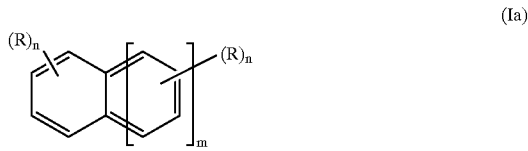
(Ia)

in which formula (Ia) m represents a number equal to 0, 1 or 2, and the symbols R are identical or different, and n representing the number of substituents on the ring.

8. A process according to claim 2, wherein the aromatic compound corresponding to formula (I) is a compound made up of a chain of two or more monocyclic aromatic carbocyclic rings corresponding to the formula (Ib):

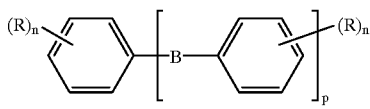

in which formula (Ib) the symbols R are identical or different, and n have the meaning given above, p is a number equal to 0, 1, 2 or 3 and B represents:

a valency bond, an alkylene or alkylidene radical having 1 to 4 carbon atoms, one of the following groups:

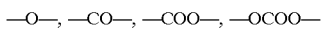

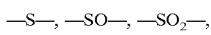

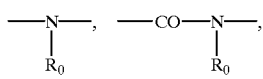

in which formulae, $R_0$ represents a hydrogen atom or an alkyl radical having 1 to 4 carbon atoms, a cyclohexyl or phenyl radical.

9. A process according to claim 2, wherein the aromatic compound corresponding to formula (I) is a monocyclic or polycyclic, aromatic carbocyclic compound having rings which can form with one another an orthocondensed system corresponding to the formula (Ia):

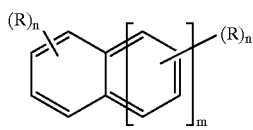

in which formula (Ia) m represents a number equal to 0, 1 or 2, and the symbols R are identical or different; or wherein the aromatic compound corresponding to formula (1) is a compound made up of a chain of two or more monocyclic aromatic carbocyclic rings corresponding to the formula (Ib):

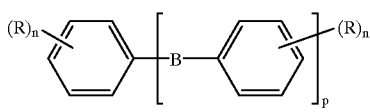

in which formula (Ib) the symbols R are identical or different, and n have the meaning given above, p is a number equal to 0, 1, 2 or 3 and B represents:

a valency bond, an alkylene or alkylidene radical having 1 to 4 carbon atoms, one of the following groups:

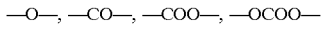

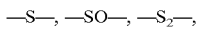

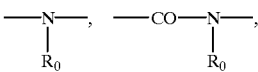

in which formulae, $R_0$ represents a hydrogen atom or an alkyl radical having 1 to 4 carbon atoms, a cyclohexyl or phenyl radical, and wherein for formulas (Ia) and (Ib), R represents a hydrogen atom, a hydroxyl group, a thiol group, a —CHO group, a $NO_2$ group, a —$NH_2$ group, a linear or branched alkyl or alkoxy radical having 1 to 6 carbon atoms, or a halogen atom, B symbolizes a valency bond, an alkylene or alkylidene radical having 1 to 4 carbon atoms or an oxygen atom, m is equal to 0 or 1, n is equal to 0, 1 or 2, p is equal to 0 or 1.

10. A process according to claim 2, wherein the aromatic compound corresponds to formula (I), wherein R represents a hydrogen atom, a hydroxyl group, a methyl radical, a methoxy radical or a halogen atom.

11. A process according to claim 1, wherein the aromatic compound is benzene, toluene, the mono- and dichlorobenzenes, fluorobenzene, iodobenzene, phenol, fluorophenol, anisole, veratrole, 1-methoxynaphthalene, 2-methoxynaphthalene.

12. A process according to claim 1, wherein the acylating agent is selected from carboxylic acids and their derivatives, halides and anhydrides, and the sulphonylating agent from sulphonyl or aminosulphonyl halides or anhydrides.

13. A process according to claim 12, wherein the acylating agent or sulphonylating agent corresponds to the following formulae:

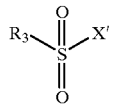

in which formulae (II) or (III):

$R_3$ represents:

a saturated or unsaturated linear or branched aliphatic radical having 1 to 24 carbon atoms; a saturated, unsaturated or aromatic, monocyclic or polycyclic cycloaliphatic radical having 4 to 12 carbon atoms; a saturated or unsaturated, linear or branched aliphatic radical which carries a cyclic substituent, X' represents:

a halogen atom, in formula (II):

X' represents a —O—CO—$R_4$ radical, where $R_4$ is identical to or different from $R_3$ and has the same meaning as $R_3$, in formula (III):

X' represents a —O—$SO_2$—$R_4$ radical with $R_4$ being identical to or different from $R_3$, having the same meaning as $R_3$, R3 represents:

a $R_5$—O— alkoxy radical with $R_5$ having the same meaning as $R_3$, a ($R_6$) ($R_7$)—N-amino group with $R_6$ which is identical to or different from $R_7$ having the same meaning as $R_3$.

14. A process according to claim 13, wherein the acylating agent corresponds to formula (II) in which X' represents a chlorine atom and $R_3$ represents a linear or branched alkyl radical having 1 to 12 carbon atoms: it being possible for the hydrocarbon chain to be optionally interrupted by a heteroatom or by a functional group or to carry a substituent; $R_3$ represents an optionally substituted phenyl radical; or X' represents an —O—CO—$R_3$ radical in which $R_3$ and $R_4$ are identical and represent an alkyl radical with 1 to 4 carbon atoms, and the sulphonylating agent corresponds to formula (III) in which X' represents a chlorine atom or a —O—$SO_2$—$R_4$ radical in which $R_4$ represents an alkyl-radical with 1 to 4 carbon atoms and $R_3$ represents a phenyl or naphthyl radical or a $R_5$—O— or ($R_6$)($R_7$)—N-radical in which $R_5$, $R_6$ and $R_7$ represent a linear or branched alkyl radical with 1 to 4 carbon atoms.

15. A process according to claim 13, wherein the acylating agent comprising:
acetyl chloride,
acetyl bromide,
monochloroacetyl chloride,
dichloroacetyl chloride,
propanoyl chloride,
isobutanoyl chloride,
pivaloyl chloride,
stearoyl chloride,
crotonyl chloride,
benzoyl chloride,
the chlorobenzoyl chlorides,
p-nitrobenzoyl chloride,
o-nitrobenzoyl chloride,
the methoxybenzoyl chlorides,
the naphthoyl chlorides,
acetic anhydride,
isobutyric anhydride,
trifluoroacetic anhydride,
benzoic anhydride,
and the sulphonylating agent comprises:
benzenesulphonyl chloride,
p-chlorobenzenesulphonyl chloride,
fluorobenzenesulphonyl chloride,
nitrobenzenesulphonyl chloride,
methoxybenzenesulphonyl chloride,
tosyl chloride,
dimethylsulphamoyl chloride,
methoxysulphonyl chloride,
benzenesulphonic anhydride,
p-toluenesulphonic anhydride.

16. A process according to claim 1, wherein the catalyst is a Lewis acid.

17. A process according to claim 1, wherein the catalyst is an organic salt, of groups (IIIa), (IVa), (VIII), (IIb), (IIIb), (IVb), (Vb) or (VIb) of the periodic table of elements.

18. A process according to claim 1, wherein the catalyst is an inorganic salt, of groups (IVa), (VIII), (IIb), (IIIb), (IVb), (Vb) or (VIb) of the periodic table of elements.

19. A process according to claim 17, wherein the salt of the elements comprises:

group (IIIa) of the periodic table;
group (IVa);
group (VIII);
group (IIb);
group (IIIb);
group (IVb),
group (Vb); or
group (VIb).

20. A process according to claim 18, wherein the catalyst comprises metallic halides.

21. A process according to claim 20, wherein the catalyst is generated in situ by using any metal or metalloid compound combined with a source of halogen.

22. A process according to claim 18, wherein the aforementioned elements are introduced in the form of a metal or in the form of an oxide or a hydroxide; of a mineral salt or an organic salt.

23. A process according to claim 20, wherein the source of halogen is halogen in molecular form; any halide of a mineral or organic acid; or any mineral or organic metal or metalloid salt which is capable of generating a halogenated form.

24. A process according to claim 20, wherein the source of halogen is chlorine or bromine; hydrochloric acid, hydrobromic acid; acetyl chloride; silicon chloride $SiCl_4$, or halogenosilanes.

25. A process according to claim 16, wherein the catalyst is a trifluoromethanesulphonic acid rare earth and/or bismuth salt.

26. A process according to claim 25, wherein the catalyst is a trifluoromethanesulphonate of a rare earth comprising the lanthanides, yttrium, scandium and their mixtures.

27. A process according to claim 1, wherein the catalyst is a Brönsted acid.

28. A process according to claim 27, wherein the catalyst comprises sulphuric acid, hydrofluoric acid, hydrochloric acid, the phosphoric acids and the polyphosphoric acids, or the sulphonic.

29. A process according to claim 16, wherein the catalyst is in supported form.

30. A process according to claim 29, wherein the support comprises the oxides of metals, clays, or from charcoals which are optionally activated by a well-known treatment with nitric acid, acetylene black, or resins.

31. A process according to claim 29, wherein the support is in the form of a powder, beads, granules, or extrudates.

32. A process according to claim 16, wherein the catalyst is zirconium chloride, ferric chloride, zinc chloride, aluminium chloride, aluminium bromide, gallium chloride, indium chloride, stannic chloride, bismuth chloride, boron trifluoride; ferrous oxide, ferric oxide, gallium oxide; cerium triflate, ytterbium triflate, scandium triflate, tin triflate, or bismuth triflate.

33. A process according to claim 1, wherein the reaction solvent is one of the reagents or an aprotic, apolar organic solvent.

34. A process according to claim 33, wherein the organic solvent comprises the halogenated or non-halogenated aliphatic or aromatic hydrocarbons.

35. A process according to claim 1, wherein the ratio between the number of moles of between the number of moles of aromatic compound and the number of moles of acylating agent varies between 0.1 and 10.

36. A process according to claim 16, wherein the amount of catalyst used is such that the ratio between the number of moles of catalyst and the number of moles of acylating agent is less than 1.0.

37. A process according to claim 1, wherein the microwave power applied is at least 10 W.

38. A process according to claim 1, wherein the microwave power applied is at most 300 W.

39. A process according to claim 37, wherein the microwave power applied is between 30 and 100 W for volatile molecules.

40. A process according to claim 1, wherein the temperature at the surface of the reaction medium is advantageously between 60° C. and 350° C.

* * * * *